(12) United States Patent
Kato et al.

(10) Patent No.: US 6,241,456 B1
(45) Date of Patent: Jun. 5, 2001

(54) WAFER INSPECTING APPARATUS AND METHOD

(75) Inventors: Tomoo Kato, Hachioji; Tatsuo Nirei, Tokyo, both of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/569,262

(22) Filed: May 11, 2000

Related U.S. Application Data

(63) Continuation of application No. PCT/JP99/06661, filed on Nov. 29, 1999.

(30) Foreign Application Priority Data

Nov. 30, 1998 (JP) ................................... 10-339331

(51) Int. Cl.$^7$ ................................................. B65G 49/07
(52) U.S. Cl. .................... 414/783; 414/936; 414/941; 414/816
(58) Field of Search .................... 414/783, 936, 414/937, 941, 816

(56) References Cited

U.S. PATENT DOCUMENTS 4,917,556 * 4/1990 Stark et al. ........................... 414/217
5,547,515 * 8/1996 Kudo et al. ......................... 414/936 X

FOREIGN PATENT DOCUMENTS

| 1-207942 | * 8/1989 | (JP) | ..................................... 414/936 |
| 6-160292 | 6/1994 | (JP) . | |
| 8-102479 | 4/1996 | (JP) . | |

* cited by examiner

*Primary Examiner*—Janice L. Krizek
(74) *Attorney, Agent, or Firm*—Frishauf, Holtz, Goodman, Langer & Chick, P.C.

(57) ABSTRACT

This invention provides a wafer inspecting apparatus which enables macroscopic inspection of the entire surface of a wafer. According to the wafer inspecting apparatus of this invention, the edge portion of a wafer 8 is held by suction with the distal ends of wafer holding portions 702 of a wafer holding arm 7, and first-time observation of the lower surface of the wafer 8 is performed. Then, the wafer 8 is transported onto a center table 6. The center table 6 is rotated through a predetermined angle. The edge portion of the wafer 8 is held by suction again with the distal ends of the wafer holding portions 702 of the wafer holding arm 7. Then, second-time observation of the lower surface of the wafer 8 is performed.

11 Claims, 3 Drawing Sheets

WAFER INSPECTING APPARATUS AND METHOD

CROSS-REFERENCE TO RELATED APPLICATIONS

This is a continuation of Application No. PCT/JP99/06661, filed Nov. 29, 1999.

This application is based upon and claims the benefit of priority from the prior Japanese Patent Application No. 10-339331, filed Nov. 30, 1998, the entire contents of which are incorporated herein by reference.

BACKGROUND OF THE INVENTION

The present invention relates to a wafer inspecting apparatus and method which enable visual macroscopic inspection of a wafer.

A wafer inspecting apparatus has conventionally been put into practical use, which can pick up a desired wafer from a wafer holder holding a plurality of wafers and macroscopically inspect the picked wafer by visual observation. For example, according to one such apparatus, a desired wafer is picked up from a wafer holder holding a plurality of wafers by a wafer pickup/return arm, and is supplied onto a macro-table. The edge portion of the lower surface of the wafer supplied onto the macro-table is held by suction with a wafer holding arm, and the wafer is turned. After the lower surface of the wafer is observed, the wafer is returned onto the macro-table, and is returned to the original position in the wafer holder with the wafer pickup/return arm.

With this wafer inspecting apparatus, upon macroscopic inspection of the upper and lower surfaces of the wafer, the lower surface of the wafer is held by suction with the wafer holding arm. In the macroscopic inspection of the lower surface, the portion held by suction with the wafer holding arm cannot be seen. Therefore, observation of the entire surface of the wafer cannot be performed, and the precision of macroscopic inspection decreases.

The present invention has been made in view of the above situation, and has as its object to provide a wafer inspecting apparatus and method which enable macroscopic inspection of the entire surface of the wafer.

BRIEF SUMMARY OF THE INVENTION

According to the first invention of the present invention, there is provided a wafer inspecting apparatus characterized by comprising wafer transfer means for picking up a desired wafer from a wafer holder holding a plurality of wafers, wafer support means thereon for supporting the wafer picked up by the wafer transfer means and rotating the supported wafer at least through a predetermined angle, wafer holding means, having a plurality of wafer holding portions extending toward a center of the wafer, for holding the wafer supported on the wafer support means by coming into contact with one surface thereof with the plurality of wafer holding portions, and turning the held wafer to observe one surface thereof, and control means for supporting the wafer on the wafer support means again, after the wafer is turned by the wafer holding means, and rotating the wafer through a predetermined angle with the wafer support means, and inverting the wafer holding means.

In this case, the plurality of wafer holding portions of the wafer holding means may hold the wafer by suction.

The control means rotates the wafer supported on the wafer support means through such a rotational angle that a moving amount larger than the width of the wafer holding portions can be obtained.

Upon observing one surface of the wafer, the control means may rotate the wafer supported on the wafer support means so that a region concealed by the plurality of wafer holding portions can be observed.

The wafer support means may be a center table of the wafer inspecting apparatus, and the control means may control the rotational angle of the center table.

According to the second invention of the present invention, there is provided a wafer inspecting method characterized by comprising picking up a desired wafer from a wafer holder holding a plurality of wafers, transporting the picked wafer onto a center table, holding the wafer transported to the center table by coming into contact with a lower surface thereof with a plurality of wafer holding portions, and turning the held wafer to observe the lower surface thereof, restoring the turned wafer to a state wherein an upper surface of the wafer faces up and then transporting the wafer to the center table so as to rotate the center table, thereby rotating the wafer transported to the center table through a predetermined angle, and holding the wafer, which has been rotated through the predetermined angle, by coming into contact with the lower surface thereof with the plurality of wafer holding portions, and turning the held wafer again to observe the lower surface thereof.

As a result, according to the present invention, after the surface of the wafer held by the wafer holding portions is observed, the wafer is supported on the wafer support means and is rotated through the predetermined angle. The wafer is held by suction with the wafer holding means again, and the surface of the wafer is observed again. Therefore, that surface of the wafer, which is unseen when the wafer is held by the wafer holding means for the first time, can be exposed when the wafer is held by the wafer holding means for the second time. As a result, the entire surface of the wafer can be thoroughly observed.

According to the present invention, since the non-inspected region concealed by the wafer holding means can be exposed again near the wafer holding means, it can be recognized easily and efficient observation can be performed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An embodiment of the present invention will be described with reference to the accompanying drawings.

Figure 1:
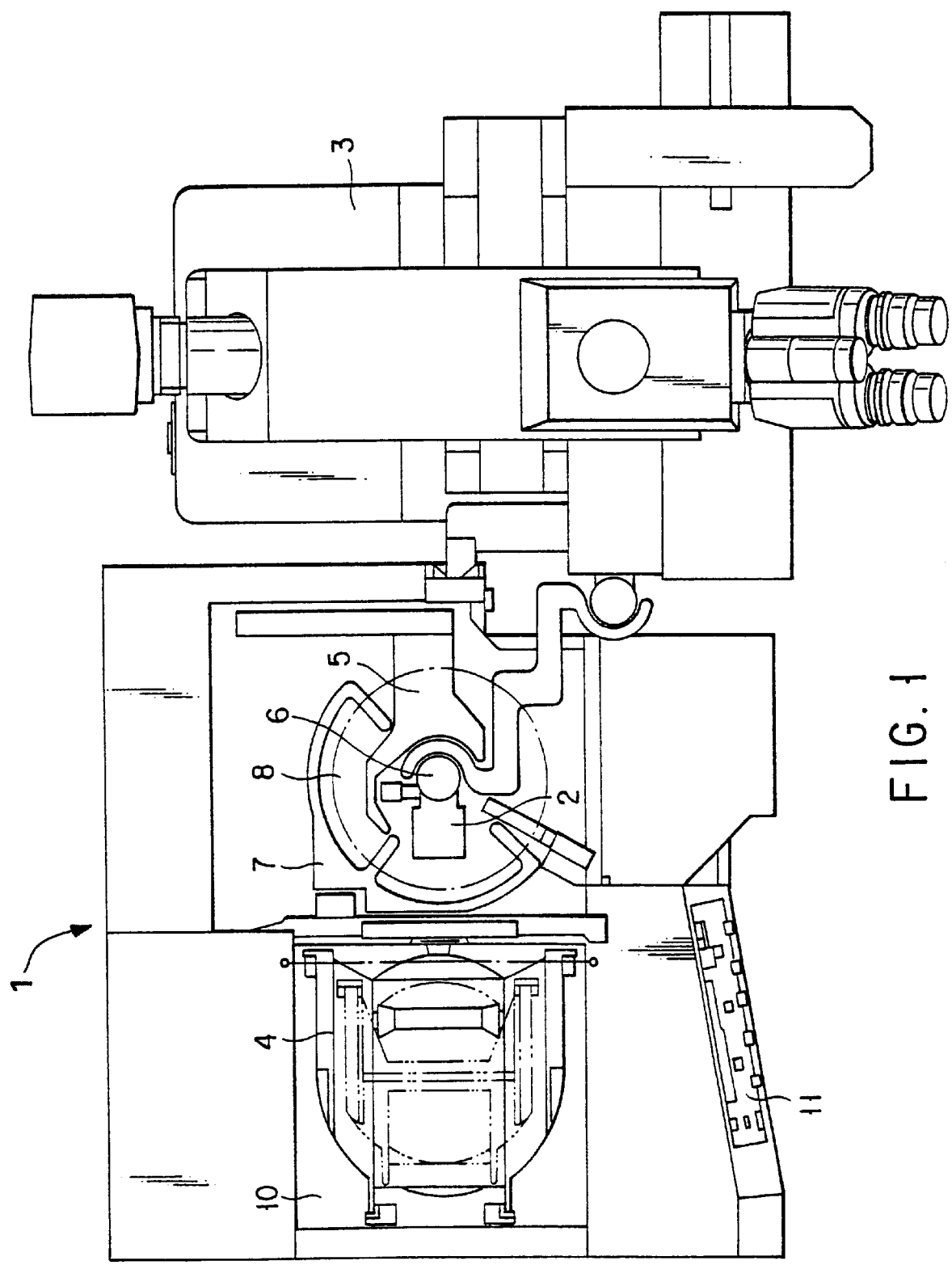
FIG. 1 is a view showing a wafer inspecting apparatus according to an embodiment of the present invention.

FIG. 1 shows the schematic arrangement of a wafer inspecting apparatus to which the present invention is applied. Referring to FIG. 1, reference numeral 1 denotes a wafer transfer apparatus main body. The apparatus main body 1 has a macroscopic inspection unit 2 for macroscopically inspecting a wafer 8 (to be described later), and an elevator mechanism section 10. Adjacent to the wafer transfer apparatus main body 1, a microscopic inspection unit 3 is arranged to microscopically inspect the selectively supplied wafer 8. In this case, the microscopic inspection unit 3 is used to observe the surface of the wafer 8 by using a microscope. The microscopic inspection unit 3 using a microscope is known, and a detailed description thereof will accordingly be omitted.

A cassette 4 which holds a plurality of wafers 8 at predetermined pitch intervals in the stacking direction is supported by the elevator mechanism section 10 to serve as a wafer holder, and can be vertically moved at predetermined pitches.

This macroscopic inspection unit 2 is provided with a wafer pickup/return arm 5 and center table 6 to oppose the cassette 4. The wafer pickup/return arm 5 serves as a wafer transfer means, and the center table 6 serves as a wafer support means. The wafer pickup/return arm 5 has a linear movable mechanism and a vertical movable mechanism. The linear movable mechanism moves forward and backward toward and from the cassette 4 along a guide (not shown). The vertical movable mechanism vertically moves at its backward position. The wafer pickup/return arm 5 can perform a series of operations. Namely, the wafer pickup/return arm 5 moves forward toward the cassette 4 to hold the wafer 8 in the cassette 4 by suction, and picks up the wafer 8 as it moves backward. As the wafer pickup/return arm 5 moves downward at the backward position, it transports the wafer 8 onto the center table 6. Also, the wafer pickup/return arm 5 holds the wafer 8 on the center table 6 by suction, moves upward once, and further moves forward toward the cassette 4 to return the wafer 8 into the cassette 4.

The center table 6 holds the wafer 8 supported on it by suction, and can pivot and rotate through a predetermined angle. In this case, the center table 6 is preferably rotatable. When observing the surface of the wafer 8 supported on the center table 6, the center table 6 allows macro-observation while rotating the wafer 8. Also, the surface of the wafer 8 can be observed in different angles through pivot operation performed by an operating mechanism (not shown). Rotation of the center table 6 through a predetermined angle is performed when observing the lower surface again, and is controlled to have an amount of rotation slightly larger than the width of wafer holding portions 702 of a wafer holding arm 7 (to be described below), in this case, about 10°. The amount of rotation of the center table 6 for inspecting the lower surface again may be controlled to such a value that a non-inspected region (unseen portion) in observation of the lower surface and the wafer holding portions 702 do not overlap.

Figure 2:
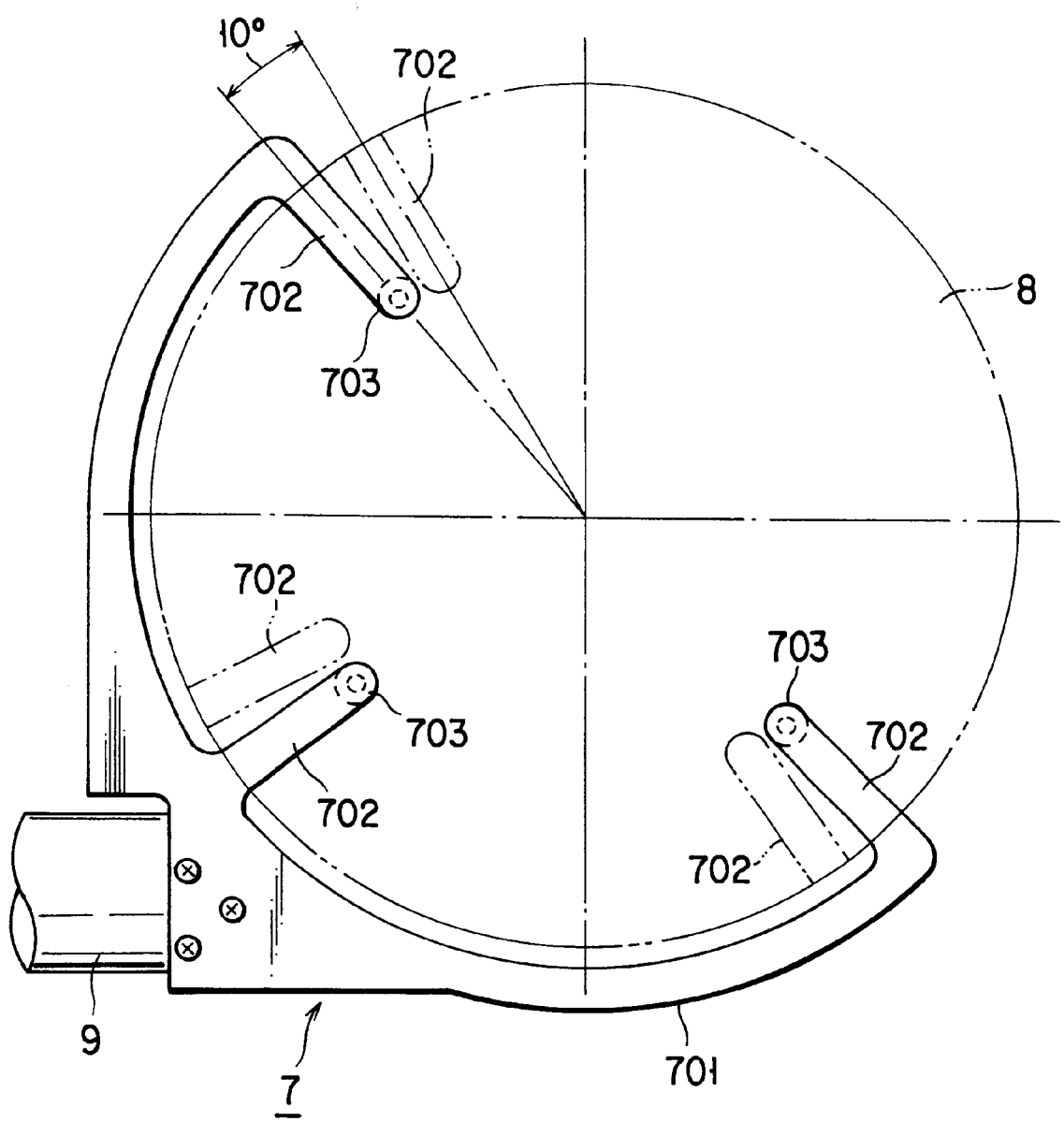
FIG. 2 is a view showing the wafer holding arm of the wafer inspecting apparatus of this embodiment.

The wafer holding arm 7 serving as the wafer holding means is arranged to surround the center table 6 of the macroscopic inspection unit 2. As shown in FIG. 2, the wafer holding arm 7 has an arcuated arm main body 701 and the plurality of (three in FIG. 2) wafer holding portions 702 equidistantly arranged along the arc of the arm main body 701. Each of the wafer holding portions 702 has a predetermined width, extends toward the center of the arc of the arm main body 701, i.e., toward the center of the wafer 8, and has a suction portion 703 using air at its distal end portion. The suction portions 703 hold the wafer 8 supported on the center table 6 by suction from the lower surface side (from below).

The wafer holding arm 7 is pivotally supported by a rotating shaft 9. When the wafer holding arm 7 is pivoted through a predetermined angle about the rotating shaft 9 as the center, it turns the held wafer 8 so that the lower surface of the wafer 8 can be observed.

The operation of the embodiment having the above arrangement will be described.

The cassette 4 holding the plurality of wafers 8 is set on the elevator mechanism section 10 of the wafer transfer apparatus main body 1.

Figure 3:
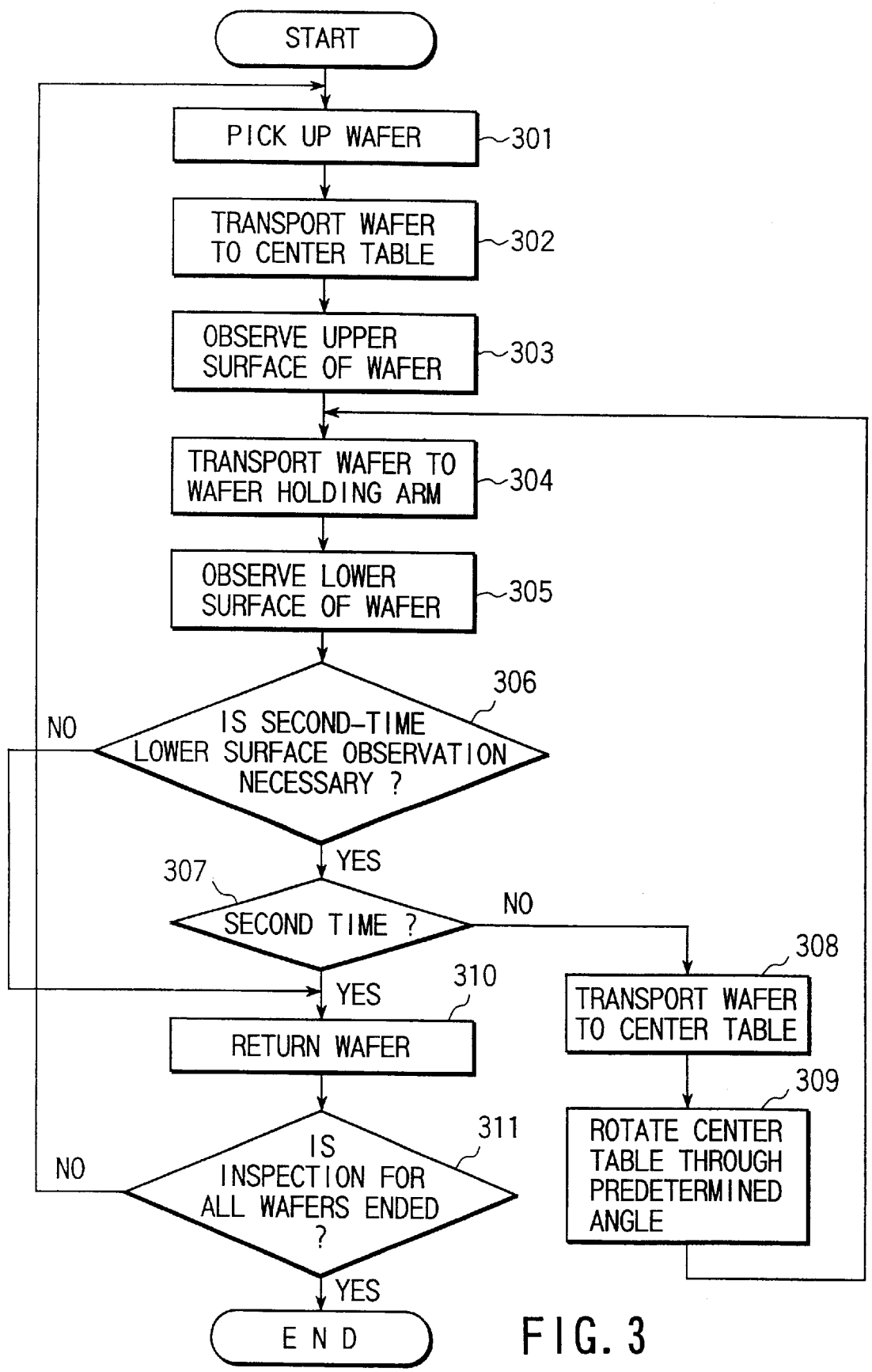
FIG. 3 is a flow chart for explaining the operation of the wafer inspecting apparatus according to this embodiment.

In this state, an operation panel 11 of the macroscopic inspection unit 2 is operated to additionally set a second-time lower surface macro-mode to the macro-mode. Then, a controller in the apparatus main body 1 performs the flow shown in FIG. 3. First, in step 301 the wafer pickup/return arm 5 moves forward toward the cassette 4 along the guide (not shown). The wafer pickup/return arm 5 holds the wafer 8 in the cassette 4 and picks it up to the outside of the cassette 4 as it moves backward. When the wafer pickup/return arm 5 moves to a predetermined backward position, it moves downward in step 302 to transport the wafer 8 onto the center table 6. In this state, in step 303 the center table 6 is pivoted by an operation mechanism (not shown), and visual macro-observation of the surface of the wafer 8 is performed.

After that, in step 304 the wafer 8 is held by suction from its lower surface with the suction portions 703 at the distal ends of the wafer holding portions 702 of the wafer holding arm 7. In step 305, the wafer holding arm 7 is pivoted through a predetermined angle about the rotating shaft 9 as the center to turn the wafer 8, and visual macro-observation of the lower surface of the wafer 8 is performed.

In step 306, whether second-time lower-surface observation need be performed is checked. Since the flow is made on the premise that the user has set the second-time lower surface macro-mode, the flow advances to the process of step 307.

In step 307, whether macroscopic inspection of the lower surface of the wafer 8 is to be performed for the second time is checked. In this case, since this macroscopic inspection is to be performed for the first time, the flow advances to step 308. The wafer 8 is released from the wafer holding arm 7 and is transported onto the center table 6. In step 309, the center table 6 is rotated through a predetermined angle. Then, the flow returns to step 304, and the wafer 8 is held again by suction from its lower surface with the suction portions 703 at the distal ends of the wafer holding portions 702 of the wafer holding arm 7. In this case, since the center table 6 is rotated through the predetermined angle, the non-inspected region on the lower surface of the wafer 8 held by suction with the wafer holding portions 702 falls under the portion indicated by a broken line in FIG. 2, which is different from the first position.

In this state, in step 305 the wafer holding arm 7 is rotated through a predetermined angle to turn the wafer 8, and visual macro-observation of the lower surface of the wafer 8 is performed again.

When it is determined in step 307 that observation of the lower surface of the wafer 8 is performed for the second time (lower surface observation is ended), the wafer 8 is released from the wafer holding arm 7 in step 310. The wafer pickup/return arm 5 holds the wafer 8 transported onto the center table 6. The wafer pickup/return arm 5 then moves upward once, and moves forward toward the cassette 4 to return the wafer 8 to the initial position in the cassette 4.

These operations are repeatedly performed until it is determined in step 311 that observation for macroscopic inspection for all or a specified wafer 8 in the cassette 4 is ended.

In this manner, after the lower surface of the wafer 8 is held by suction with the distal ends of the wafer holding portions 702 of the wafer holding arm 7, and first-time observation of the lower surface of the wafer 8 is performed, the wafer 8 is transported onto the center table 6. The center table 6 is rotated through the predetermined angle, and the lower surface of the wafer 8 is held by suction again with the distal ends of the wafer holding portions 702 of the wafer holding arm 7, so that second-time observation of the lower surface of the wafer 8 is performed. Therefore, that portion on the edge portion of the wafer 8 which is to be held by suction with the wafer holding arm 7 can be set at different positions between the first time and the second time. The lower surface of the wafer 8, which is unseen when the wafer is held by suction for the first time with the wafer holding portions 702, can be exposed when the wafer is held by suction for the second time with the wafer holding portions 702. As a result, the entire surface of the wafer 8 can be thoroughly observed, and the precision of macroscopic inspection can be improved greatly.

The center table 6 is controlled to have such a rotational angle that a moving amount slightly larger than the width of the wafer holding portions 702 of the wafer holding arm 7, which extend toward the center of the wafer, can be obtained. Therefore, the non-inspected region can be positioned near the wafer holding portions 702. The non-inspected region can accordingly be recognized easily, and efficient observation can be performed.

In the embodiment described above, the wafer holding arm 7 holds the edge portion of the wafer 8 by suction from its lower side with the suction portions 703 at the distal ends of its wafer holding portions 702. This wafer holding arm 7 can also hold the edge portion of the wafer 8 by suction from the upper side. Also, the wafer holding arm 7 can hold the wafer 8 by supporting it thereon.

As described above, according to the present invention, the edge portion of the wafer, which is unseen when the wafer is held by the wafer holding means for the first time, can be exposed when the wafer is held by the wafer holding means for the second time. As a result, the entire surface of the wafer can be thoroughly observed, and the precision of macroscopic inspection can be improved greatly.

Since the non-inspected region concealed by the wafer holding means can be exposed again near the wafer holding means, it can be recognized easily and efficient observation can be performed.

As has been described above, the wafer inspecting apparatus and method according to the present invention are appropriate for performing visual macroscopic inspection of the wafer.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A wafer inspecting apparatus comprising:
    wafer transfer means for picking up a desired wafer from a wafer holder holding a plurality of wafers;
    wafer support means for supporting the wafer picked up by said wafer transfer means, and rotating the supported wafer at least through a predetermined angle;
    wafer holding means, having a plurality of wafer holding portions extending toward a center of the wafer, for holding the wafer supported on said wafer support means by coming into contact with a lower surface of the wafer with said plurality of wafer holding portions, and turning the held wafer to observe the lower surface of the wafer; and
    control means for causing the wafer holding means to turn the held wafer to observe the lower surface of the wafer, causing the wafer holding means to release the turned wafer on the wafer support means, causing the wafer support means to rotate the released wafer through a predetermined angle, and causing the wafer holding means to turn the rotated wafer to observe the lower surface of the wafer again.

2. A wafer inspecting apparatus according to claim 1, wherein said plurality of wafer holding portions of said wafer holding means hold the wafer by suction.

3. A wafer inspecting apparatus according to claim 1, wherein said control means controls said wafer support means to rotate the wafer supported on said wafer support means through a rotational angle such that a moving amount larger than a width of said wafer holding portions is obtained.

4. A wafer inspecting apparatus according to claim 1, wherein, upon observing of the lower surface of the wafer, said control means controls said wafer support means to rotate the wafer supported on said wafer support means so that a region concealed by said plurality of wafer holding portions is observed.

5. A wafer inspecting apparatus according to claim 1, wherein said wafer support means comprises a center table of said wafer inspecting apparatus, and said control means controls a rotational angle of said center table.

6. A wafer inspecting method comprising:
    picking up a desired wafer from a wafer holder holding a plurality of wafers;
    transporting the picked up wafer onto a center table;
    holding the wafer transported onto said center table by coming into contact with a lower surface of the wafer with a plurality of wafer holding portions, and turning the held wafer to observe the lower surface of the wafer;
    restoring the turned wafer to a state wherein an upper surface of the wafer faces up and then transporting the wafer onto said center table;
    rotating said center table so as to rotate the wafer transported onto said center table through a predetermined angle; and
    holding the wafer, which has been rotated through the predetermined angle, by coming into contact with the lower surface of the wafer with said plurality of wafer holding portions, and turning the held wafer again to observe the lower surface of the wafer.

7. A wafer inspecting apparatus comprising:
    a wafer transfer member adapted to pick up a desired wafer from a wafer holder holding a plurality of wafers;
    a wafer support member that supports the wafer picked up by said wafer transfer member, and rotates the supported wafer at least through a predetermined angle;
    a wafer holding member, having a plurality of wafer holding portions extending toward a center of the wafer, that holds the wafer supported on said wafer support member by coming into contact with a lower surface of the wafer with said plurality of wafer holding portions, and turns the held wafer to observe a lower surface of the wafer; and a controller that causes said wafer holding member to turn the held wafer to observe the lower surface of the wafer, causes said wafer holding member to release the turned wafer on said wafer support member, causes said wafer support member to rotate the released wafer through a predetermined angle, and causes said wafer holding member to turn the rotated wafer to observe the lower surface of the wafer again.

8. A wafer inspecting apparatus according to claim 7, wherein said plurality of wafer holding portions of said wafer holding member hold the wafer by suction.

9. A wafer inspecting apparatus according to claim 7, wherein said controller controls said wafer support member to rotate the wafer supported on said wafer support member through a rotational angle such that a moving amount larger than a width of said wafer holding portions is obtained.

10. A wafer inspecting apparatus according to claim 7, wherein, upon observing of the lower surface of the wafer, said controller controls said wafer support member to rotate the wafer supported on said wafer support member so that a region concealed by said plurality of wafer holding portions is observed.

11. A wafer inspecting apparatus according to claim 7, wherein said wafer support member comprises a center table of said wafer inspecting apparatus, and said controller controls a rotational angle of said center table.

* * * * *